United States Patent
Blumenkranz et al.

(10) Patent No.: US 10,492,871 B2
(45) Date of Patent: Dec. 3, 2019

(54) FIBER MANAGEMENT IN MEDICAL INSTRUMENT BACKEND

(71) Applicant: INTUITIVE SURGICAL OPERATIONS, INC., Sunnyvale, CA (US)

(72) Inventors: Stephen J. Blumenkranz, Los Altos Hills, CA (US); Vincent Duindam, San Francisco, CA (US); Mark E. Froggatt, Blacksburg, VA (US); Eric E. Sanborn, Blacksburg, VA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/570,912

(22) PCT Filed: Apr. 29, 2016

(86) PCT No.: PCT/US2016/030275
§ 371 (c)(1),
(2) Date: Oct. 31, 2017

(87) PCT Pub. No.: WO2016/179039
PCT Pub. Date: Nov. 10, 2016

(65) Prior Publication Data
US 2018/0228548 A1     Aug. 16, 2018

Related U.S. Application Data

(60) Provisional application No. 62/155,655, filed on May 1, 2015.

(51) Int. Cl.
*A61B 34/20* (2016.01)
*G02B 6/36* (2006.01)
(Continued)

(52) U.S. Cl.
CPC ............ *A61B 34/20* (2016.02); *A61B 1/0051* (2013.01); *A61B 1/07* (2013.01); *A61B 5/065* (2013.01);
(Continued)

(58) Field of Classification Search
None
See application file for complete search history.

(56) References Cited

U.S. PATENT DOCUMENTS

| 2,672,378 A | 3/1954 | McVey |
| 2,983,553 A | 5/1961 | Dexter |

(Continued)

FOREIGN PATENT DOCUMENTS

WO   WO-2014201501 A1   12/2014

OTHER PUBLICATIONS

International Preliminary Report on Patentability for Application No. PCT/US2016/030275, dated Nov. 16, 2017, 7 pages.

(Continued)

*Primary Examiner* — Michelle R Connelly
(74) *Attorney, Agent, or Firm* — Haynes and Boone, LLP (57) ABSTRACT

A flexible tool comprising an optical fiber and a rigid member. The optical fiber includes a proximal end, a distal end, an intermediate portion between the proximal end and the distal end, and an adjustable bend between the proximal end and the intermediate portion. The intermediate portion is fixed within the rigid member, wherein the rigid member is substantially a cylinder with a flat surface along an axial length of the cylinder, and wherein the intermediate portion is constrained to have a single degree of freedom that is translational substantially along an axis defined by the optical fiber at the intermediate portion.

18 Claims, 10 Drawing Sheets

(51) Int. Cl.
*A61B 1/07* (2006.01)
*A61B 1/01* (2006.01)
*G02B 23/26* (2006.01)
*A61B 5/06* (2006.01)
*A61B 1/005* (2006.01)
*A61B 34/30* (2016.01)
*A61B 1/00* (2006.01)
*A61M 25/01* (2006.01)

(52) U.S. Cl.
CPC ............... *G02B 6/36* (2013.01); *G02B 23/26* (2013.01); *A61B 1/00165* (2013.01); *A61B 2034/2061* (2016.02); *A61B 2034/301* (2016.02); *A61M 2025/0166* (2013.01)

(56) References Cited

U.S. PATENT DOCUMENTS

| | | | |
|---|---|---|---|
| 3,751,139 | A | 8/1973 | Malherbe |
| 4,065,188 | A | 12/1977 | Ridler et al. |
| 4,262,974 | A | 4/1981 | Tojo et al. |
| 4,268,123 | A | 5/1981 | Mesco |
| 5,201,584 | A | 4/1993 | Simons |
| 5,268,986 | A * | 12/1993 | Kakii .................... G02B 6/4441 385/135 |
| 7,720,322 | B2 | 5/2010 | Prisco |
| 7,781,724 | B2 | 8/2010 | Childers et al. |
| 8,183,520 | B2 * | 5/2012 | Prisco .................... G01B 11/18 250/227.14 |
| 8,460,236 | B2 | 6/2013 | Roelle et al. |
| 8,672,837 | B2 | 3/2014 | Roelle et al. |
| 9,138,166 | B2 | 9/2015 | Wong et al. |
| 9,974,617 | B2 * | 5/2018 | Flexman ............ G02B 23/2476 |
| 2004/0158159 | A1 * | 8/2004 | Seto ..................... A61B 1/0051 600/476 |
| 2007/0156019 | A1 * | 7/2007 | Larkin .................... B25J 19/025 600/104 |
| 2008/0285909 | A1 * | 11/2008 | Younge ................ A61B 5/1076 385/13 |
| 2010/0202727 | A1 | 8/2010 | Prisco |
| 2011/0113852 | A1 * | 5/2011 | Prisco .................... G01B 11/18 73/1.15 |
| 2011/0224825 | A1 * | 9/2011 | Larkin .................... B25J 19/025 700/254 |
| 2013/0296695 | A1 * | 11/2013 | Spencer ............... A61B 5/0062 600/425 |
| 2014/0275997 | A1 | 9/2014 | Chopra et al. |
| 2014/0276937 | A1 | 9/2014 | Wong et al. |
| 2015/0079218 | A1 * | 3/2015 | Ohara ................ A61B 1/00165 425/383 |
| 2015/0231287 | A1 * | 8/2015 | Lin .......................... A61L 2/10 607/80 |
| 2016/0038000 | A1 * | 2/2016 | Miyahara ............... G02B 6/444 600/110 |
| 2016/0374590 | A1 * | 12/2016 | Wong ..................... A61B 5/065 600/424 |
| 2017/0020612 | A1 * | 1/2017 | Kuboi .................... G02B 23/26 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Search Report for PCT/US2016/030275, dated Aug. 19, 2016, 3 pages.
Written Opinion of the ISA for PCT/US2016/030275, dated Aug. 19, 2016, 5 pages.

* cited by examiner

FIBER MANAGEMENT IN MEDICAL INSTRUMENT BACKEND

This application is the U.S. national phase of International Application No. PCT/US2016/030275 filed 29 Apr. 2016, which designated the U.S. and claims to the benefit of U.S. Provisional Patent Application No. 62/155,655, the entire contents of each of which are hereby incorporated by reference.

BACKGROUND

Various techniques for detecting the shape of an optical fiber and application thereof are known.

U.S. Pat. No. 7,781,724, which is hereby incorporated by reference in its entirety, discloses fiber optic sensors that are capable of determining position and shape of an object. This patent discloses a fiber optic position and shape sensing device that employs an optical fiber means comprising at least two fiber cores and having an array of fiber Bragg gratings disposed therein coupled with a frequency domain reflectometer and a method for determining position and shape of an object using the fiber optic position and shape sensing device.

U.S. Pat. No. 7,720,322, which is hereby incorporated by reference in its entirety, discloses a shape sensing system with an optical fiber to determine the position and orientation of one link with respect to another link in a kinematic chain. As joints in the kinematic chain move, an interrogator sense strain in the optical fiber. The sensed strain is used to output a Cartesian position and orientation.

U.S. Pat. No. 8,460,236, which is hereby incorporated by reference in its entirety, discloses a method, system, and apparatus for sensing or measuring the shape or position and shape of one or more parts of a shapeable elongate medical instrument.

U.S. Pat. No. 8,672,837, which is hereby incorporated by reference in its entirety, also discloses a method, system, and apparatus for sensing or measuring the shape or position and shape of one or more parts of a shapeable elongate medical instrument.

BRIEF SUMMARY

Shape sensing using an optical fiber may be useful in an application where the shape and/or location of a tool needs to be known. For example, medical instruments are often inserted into a human or animal body and routed through a blood vessel or the digestive tract. The shape or position of the tool may provide useful information for the procedure using the tool. Although a catheter is frequently discussed herein, it will be appreciated that the forgoing description may be applicable to any type of tool that flexes and/or changes shape. Indeed, the present disclosure may be applied to any structure where the shape or end point location is of interest. For example, an articulated robotic arm may flex and/or change shape. The present disclosure could be applied to other flexible structures such as morphing antennas, morphing wings, tethers for remote operated vehicles and sonar arrays. Indeed, any structure where the shape or end point location is of interest could be considered a tool according to the present technology.

Figure 1:
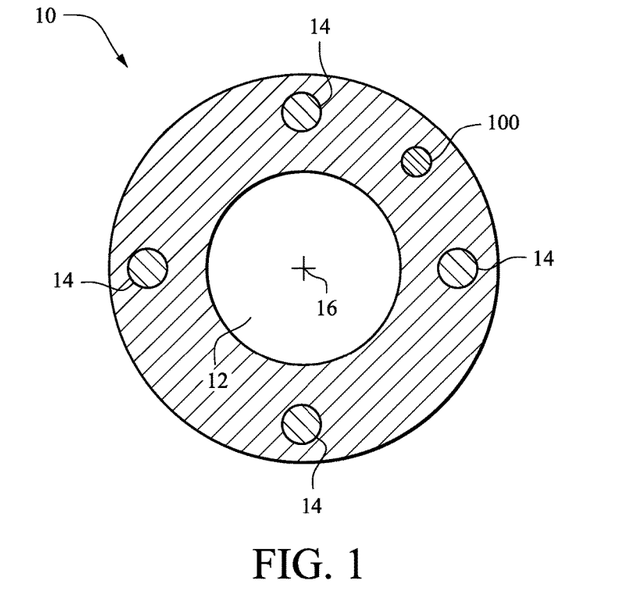
FIG. 1 is an end section view of a flexible tool with an optical fiber.

With a practical implementation of shape sensing using an optical fiber within a tool, the central portion of the tool may be used for functional aspects of the tool. For example, FIG. 1 illustrates a cross-sectional or end view of a tool 10 which will be described as a catheter. The central portion of the catheter 10 is a lumen 12 that allows for passage of another tool or substance through the catheter 10. The catheter 10 may include one or more wires 14 arrayed around the lumen 12 to manipulate the shape of the catheter 10. The locations of the lumen 12 and wires 14 may dictate that an optical fiber 100 used to sense a shape of the catheter 10 is offset from the center or neutral axis 16 of the catheter 10.

In some applications, an end of the optical fiber 100 may be fixed relative to the end of the catheter 10. For example, if a location of the end of the catheter needs to be detected, then it may be advantageous to fix an end of the optical fiber 100 with respect to the end of the catheter 10. Other reasons may exist to fix an end of the optical fiber 100 with respect to the end of the catheter 10. For example, the end of the optical fiber 100 may be the most convenient location to attach the optical fiber 100 to the catheter 10.

Figure 2:
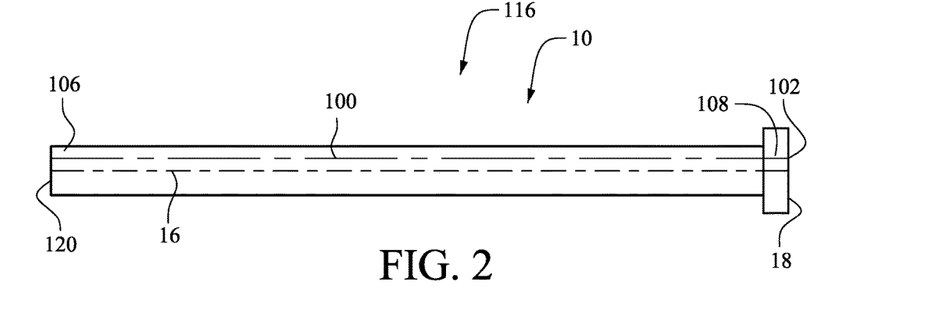
FIG. 2 is a side view of a flexible tool with an optical fiber in a straight condition.

If the optical fiber 100 is offset from the neutral axis 16, certain considerations may arise. For example, FIG. 2 illustrates a side view of a catheter 10 with the optical fiber 100 shown as a dashed line offset from the center of the catheter 10. When the catheter 10 is straight, a length of the optical fiber 100 corresponding to the length of the catheter 10 is axially aligned with the length of the catheter 10.

Figures 3, 4:
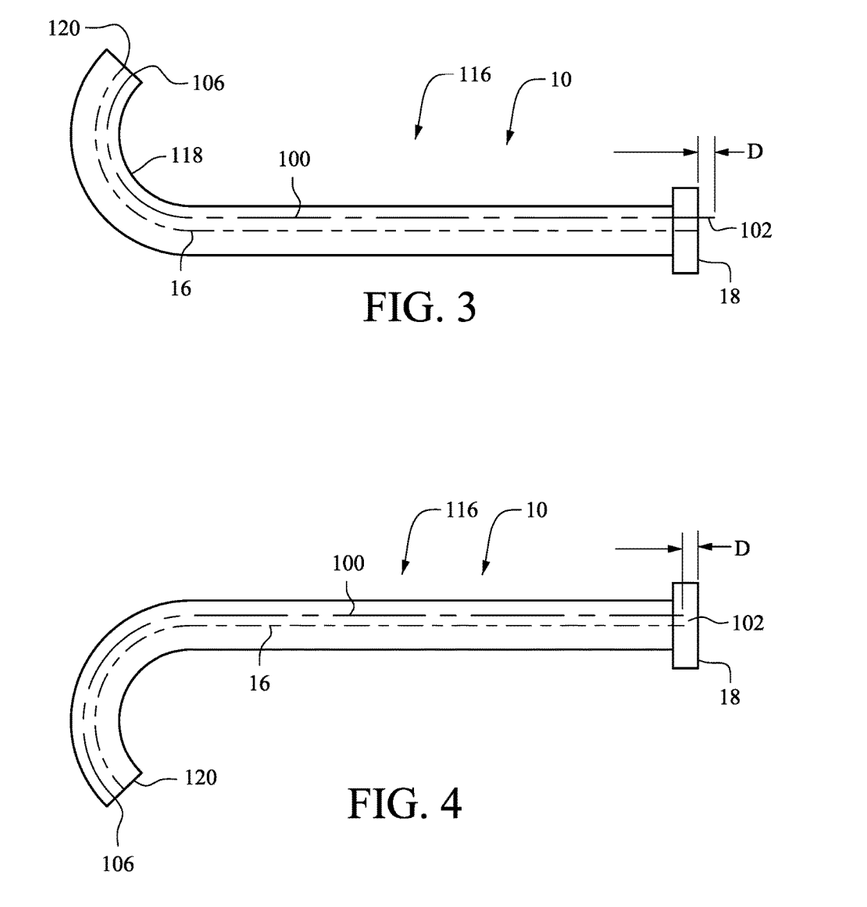
FIG. 3 is a is a side view of a flexible tool with an optical fiber in a bent condition.
FIG. 4 is a is a side view of a flexible tool with an optical fiber in a bent condition opposite to the bend in FIG. 3.

FIG. 3 illustrates the catheter 10 bent upwards or from the neutral axis 16 towards the optical fiber 100. With a bend in this direction, because the length of the optical fiber 100 does not change, a location 102 of the optical fiber 100 corresponding to an end of the catheter 10 is forced outward with respect to the end of the catheter 10 a distance D.

FIG. 4 illustrates the catheter 10 bent in a direction opposite that illustrated in FIG. 3. With such a bend, the location 102 of the optical fiber 100 is drawn into the catheter 10 a distance D.

Figure 5:
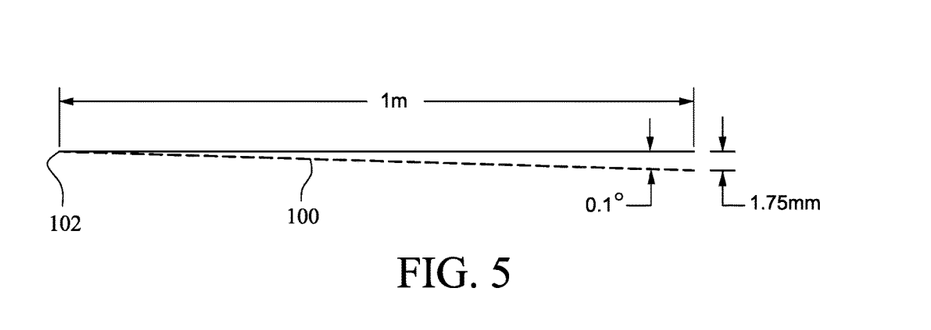
FIG. 5 is an exemplary illustration of positional error of an optical fiber.

As these figures illustrate, the optical fiber 100 moves along its length relative to the catheter 10 as the catheter 10 changes shape. Thus the shape of the fiber may not correspond exactly to a shape of the catheter 10 (e.g., because bend radii may be different and a portion of the optical fiber 100 may extend from or be drawn into the catheter 10) and a correlation may be applied to account for any differences. However, the way that the optical fiber 100 is constrained to the catheter 10 may affect the correlation. For example, as illustrated in FIG. 5, if the optical fiber is one meter long and the location 102 of the fiber 100 is misaligned with the catheter 10 by one tenth of a degree, any sensed position of an end of the catheter 10 will be off by 1.75 millimeters. If the catheter 10 and optical fiber 100 have any bends, the error may be amplified.

Also it may be important to limit the strain applied to the optical fiber 100. For example, as explained in one or more of the above-referenced patents, strain in the optical fiber 100 is used to determine the shape of the optical fiber 100. If the optical fiber 100 is stretched due being fixed to the catheter 10 (instead of or in addition to bending to conform to the shape of the catheter 10), the strain from the stretching may induce strain that affects the signal used to calculate the shape of the optical fiber 100. Also, from a mechanical perspective, too much strain placed on the optical fiber 100 could cause the fiber to break.

An aspect of the present technology solves one or more problems of the prior art.

An aspect of the present technology includes a flexible tool comprising: an optical fiber including a proximal end, a distal end, an intermediate portion between the proximal end and the distal end and an adjustable bend between the proximal end and the intermediate portion, wherein the intermediate portion is constrained to have a single degree of freedom that is translational substantially along an axis defined by the optical fiber at the intermediate portion.

In examples, (a) the flexible tool further comprises a body including a flexible portion and a free end, wherein a portion of the optical fiber is within the body and the distal end is fixed relative to the body at or near the free end; (b) the body includes a neutral axis and the optical fiber is disposed within the body offset from and substantially parallel to the neutral axis at least at the flexible portion; (c) the distal end is movable with three degrees of translational freedom with respect to the proximal end; (d) the distal end is movable with two degrees of rotational freedom with respect to the proximal end; (e) the distal end is movable with three degrees of translational freedom and two degrees of rotational freedom with respect to the proximal end; (f) the flexible portion includes a flexible joint; (g) the flexible tool further comprises a rigid member, wherein the intermediate portion is fixed within the rigid member; (h) the rigid member is substantially a cylinder with a flat surface along an axial length of the cylinder; (i) the flexible tool further comprises two cylindrical pins with central axes that are substantially parallel to one another and together define a first plane, a third cylindrical pin with a central axis that is in a second plane that is substantially parallel to and offset from the central axes of the two cylindrical pins and that is substantially normal to the first plane, a ball, and a spring, wherein the third pin and the ball contact the rigid member along the flat surface, the two cylindrical pins contact the rigid member along the axial length of the cylinder but not on the flat surface, and the spring contacts the rigid member to urge the rigid member into contact with the two cylinders, the third cylinder and the ball; (j) the rigid member comprises a block with a first flat surface defined by a first plane and a second flat surface defined by a second plane that intersects the first plane along a line that is substantially parallel to the single degree of freedom; (k) the flexible tool further comprises a support member with three spherical points of contact that contact the first flat surface, two spherical points of contact that contact the second flat surface and an urging member that urges the first flat surface and second flat surface into respective contact with the three spherical points of contact and the two spherical points of contact; (l) the rigid member includes a third flat surface substantially parallel to the first flat surface and a fourth flat surface substantially parallel to the second flat surface, and the urging member includes a first member that contacts the third flat surface to urge the rigid member towards the three spherical points of contact and a second member that contacts the fourth flat surface to urge the rigid member towards the two spherical points of contact; (m) the flexible tool further comprises a return mechanism that is configured to urge the intermediate portion towards a predetermined starting location; (n) the return mechanism is the adjustable bend and the adjustable bend comprises a loop; (o) the return mechanism comprises an electromagnet; (p) the optical fiber is connected at the proximal end to an electronic device that detects a shape of the optical fiber by transmitting light through the optical fiber; and/or (q) the flexible tool further comprises a housing that encloses the adjustable bend and provides space within the housing for the adjustable bend to adjust.

An aspect of the present technology includes a method for detecting a shape of a flexible tool, the method comprising: disposing an optical fiber along at least a portion of the flexible tool, fixing a first end of the optical fiber at or near an end of the tool, fixing a second end of optical fiber at a known position, constraining a portion of the optical fiber between the first end and the second end to a single degree of translational freedom substantially along an axis defined by the optical fiber, moving at least the end of the tool so that the tool has a resultant shape, transmitting light along the cable, and detecting the resultant shape of the flexible tool using the transmitted light.

In an example, the optical fiber is disposed offset from and substantially parallel to a neutral axis of the flexible tool.

An aspect of the present technology includes a flexible tool comprising: an optical fiber including a proximal end, a distal end, an intermediate portion between the proximal end and the distal end, an adjustable bend between the proximal end and the intermediate portion; and a housing that encloses the adjustable bend and provides space within the housing for the adjustable bend to adjust.

In examples, (a) the housing prevents contact with the adjustable bend from exterior to the flexible tool; (b) the adjustable bend includes at least one complete loop; (c) the adjustable bend is less than one complete loop; (d) the housing provides a clearance to allow relative bending and straightening of the adjustable bend; (e) the flexible tool is configured to bend a predetermined positive angle within the intermediate portion and a predetermined negative angle within the intermediate portion; and the clearance accommodates an entire extent of relative bending and straightening within the adjustable bend that is caused by bending the flexible tool the predetermined positive angle and the predetermined negative angle; (f) the space within the housing is sufficient to provide radial clearance around an entire perimeter of the adjustable bend along a predetermined length of the adjustable bend; and/or (g) the space within the housing constrains the adjustable bend to be substantially within a plane.

Other aspects, features, and advantages of this technology will become apparent from the following detailed description when taken in conjunction with the accompanying drawings, which are a part of this disclosure and which illustrate, by way of example, principles of this technology.

DETAILED DESCRIPTION

The following description is provided in relation to several examples which may share common characteristics and features. It is to be understood that one or more features of any one example may be combinable with one or more features of the other examples. In addition, any single feature or combination of features in any of the examples may constitute additional examples.

Throughout this disclosure, terms such as first, second, etc. may be used. However, these terms are not intended to be limiting or indicative of a specific order, but instead are used to distinguish similarly described features from one another, unless expressly noted otherwise. Terms such as substantially and about are intended to allow for variances to account for manufacturing tolerances, measurement tolerances, or variations from ideal values that would be accepted by those skilled in the art.

As discussed herein, a neutral axis refers to a line along a flexible body where the length does not change when the body is flexed. In a cylinder, the neutral axis coincides with the axis defining the center of the cylinder.

Figure 6:
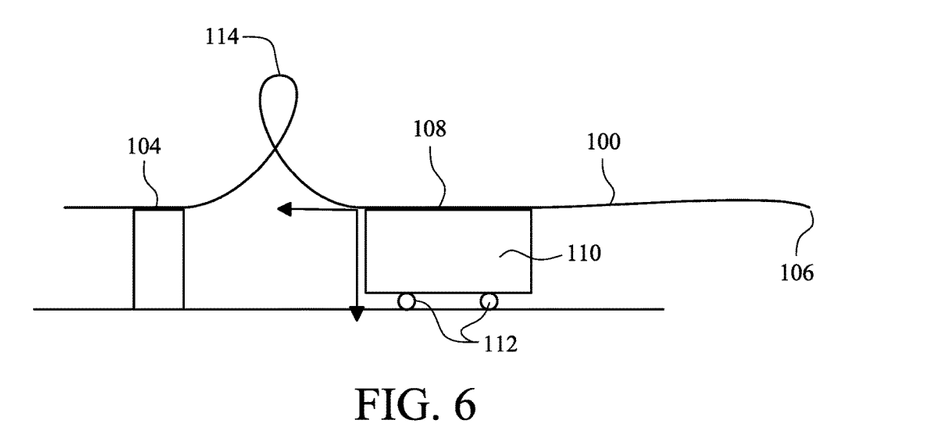
FIG. 6 is a schematic representation of an optical fiber with a proximal end, a distal end and an intermediate portion.

FIG. 6 is a schematic representation of an optical fiber 100 with a proximal end 104, a distal end 106 and an intermediate portion 108. The proximal end 104 may be fixed in place to provide a known location for calculating the shape of the optical fiber 100. The intermediate portion may have a single degree of freedom that is translational substantially along an axis defined by the optical fiber 100 at the intermediate portion 108. This single degree of freedom is schematically illustrated by a block 110 on two wheels 112. Exemplary implementations of the single degree of freedom are described in detail hereinafter.

The optical fiber 100 includes an adjustable bend 114 between the proximal end 104 and the intermediate portion 108. The adjustable bend 114 is illustrated as a loop, but a loop is not required. See, e.g., FIG. 15. The optical fiber 100 may be disposed within a body 116 that has a flexible portion 118 and a free end 120, such as the catheter 10 illustrated in FIG. 3. Not all of the optical fiber 100 needs to be within the body 116. For example, only the distal end 106 and the intermediate portion 108 could be within the body 116.

As illustrated in FIGS. 2-4, the distal end 106 may be fixed relative to the free end 120. In other words, the distal end 106 and the free end 120 move together when the body 116 is moved, for example when the flexible portion 118 is bent.

FIGS. 1-4 also illustrate the optical fiber 100 being disposed within the body 116 and offset from a neutral axis 16. By maintaining the relative position of the optical fiber 100 with respect to the neutral axis 16 for some distance, the optical fiber 100 may be substantially parallel to the neutral axis. FIGS. 3 and 4 illustrate the optical fiber 100 equidistant from the neutral axis 16 through the flexible portion 118. Thus at least when the flexible portion 118 is straight, the optical fiber 100 is substantially parallel to the neutral axis 16 at the flexible portion.

The bends illustrated in FIGS. 3 and 4 at the flexible portion 118 are necessarily two-dimensional because they are the representation of a three-dimensional object in a two-dimensional medium, but one will appreciate how the bend can occur in any direction, which will result in two degrees of both translational and rotational freedom. Also, if the body 116 is moved along the neutral axis, a third degree of translational freedom can be envisioned. Moreover, the body 116 could be twisted about the neutral axis for a third degree of rotational freedom.

Figure 7:
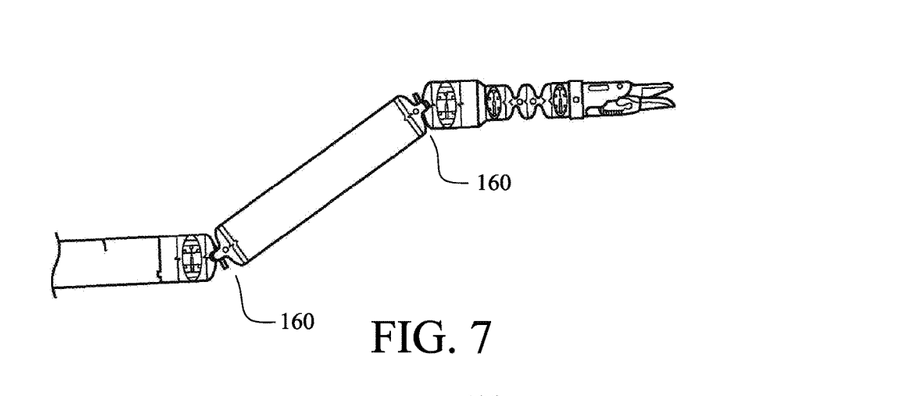
FIG. 7 is an exemplary illustration of a tool with an articulated joint.

Although the body 116 and bend at the flexible portion 118 are illustrated as continuous, the bend could be an articulated joint 160 as illustrated in FIG. 7.

Figure 8:
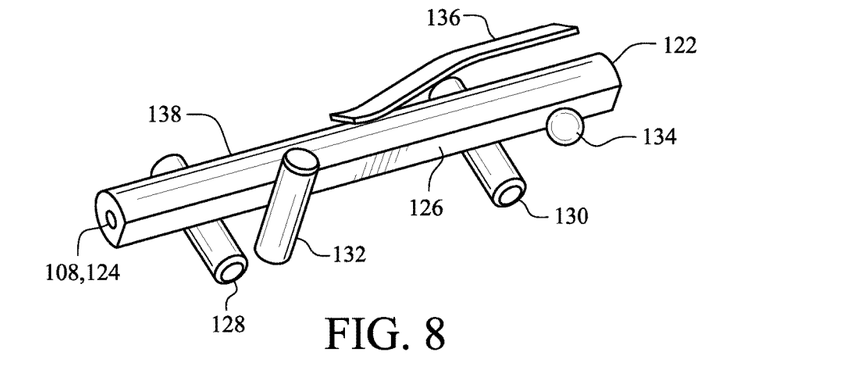
FIG. 8 is a first manner to provide a single translational degree of freedom.

FIG. 8 illustrates a first manner in which the intermediate portion 108 may be constrained to a single degree of freedom. FIG. 8 illustrates a rigid member 122 where the intermediate portion 108 is constrained within an interior portion 124 illustrated as a hole along a central axis of the rigid member 122.

As can be seen in FIG. 8, the rigid member 122 is substantially in the form of a cylinder with a flat 126 formed along an axial length of the cylinder. The rigid member 122 is supported by first and second cylindrical pins 128, 130 that contact the cylindrical surface 138 of the rigid member. The rigid member is further supported along the flat 126 by a third cylindrical pin 132 and a ball 134. A spring 136 urges the rigid member 122 into contact with the three pins 128, 130, 132 and ball 134. With this configuration, the rigid member, and thus the optical fiber 100 contained therein, can only move along the central axis of the rigid member 122, which results in a single translational degree of freedom. Although cylindrical pins are discussed throughout this document, partial cylinders or partially cylindrical surfaces may be used as well.

With the configuration illustrated in FIG. 8, the rigid member 122 is constrained by three points of contact on the flat 126 by way of the third cylindrical pin 132 and ball 134 and constrained by two points of contact on the cylindrical surface 138 by way of the first and second cylindrical pins 128, 130. With an ideal or perfectly created part, the third cylindrical pin 132 would contact the flat 126 along a line. However, due to the imperfect nature of manufactured parts, the flat 126 likely will not be perfectly flat and the third cylindrical pin 132 likely will not be perfectly round. Thus the actual contact between the flat 126 and the third cylindrical pin 132 should be two or more points of contact along the line of contact that would be present if the parts were perfectly manufactured. Thus contact between the flat 126 and the third cylindrical pin 132 is at least two points.

With the three points of contact on the flat 126, the rigid member 122 is constrained to move only in a plane defined by those three points. When the two points of contact between the rigid member 122 and the first and second cylindrical pins 128, 130 are added, the rigid member 122 is constrained to move only in a single degree of translational freedom. All rotation is prevented.

Another exemplary way to achieve a single degree of freedom is illustrated in FIGS. 9-13.

Figure 9:
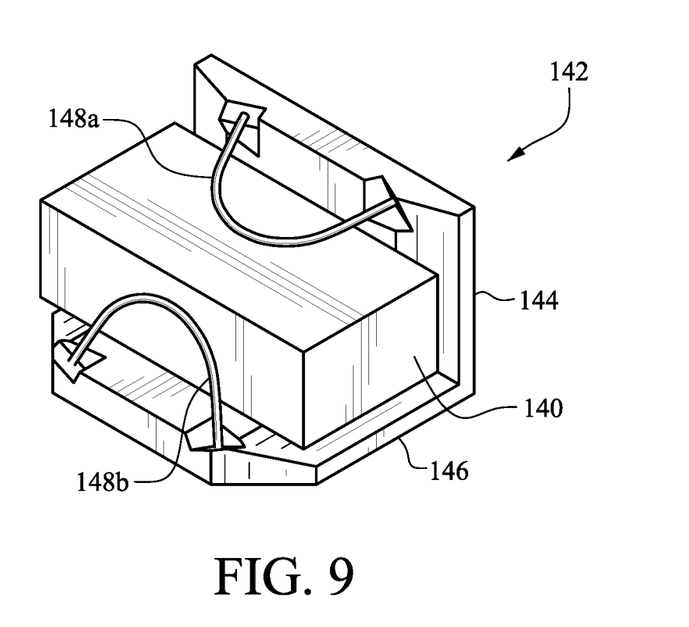
FIG. 9 is a first view of a second manner to provide a single translational degree of freedom.

FIG. 9 illustrates a perspective view of a block 140 constrained by a support member 142, which is illustrated as a rectangular prism with three pairs of parallel sides. The base 142 includes a first wall 144, a second wall 146 and an urging member illustrated as a first urging member 148a and a second urging member 148b. The first and second urging member 148a, 148b are illustrated as a U-shaped cantilevered spring that urge the block 140 towards the first wall 144 and second wall 146. Any device that tends to urge the block 140 towards the first wall 144 and second wall 146 could be employed. For example, two coil springs could be employed or a single spring oriented so that a component of the applied force is towards the first wall 144 and a second component is towards the second wall 146 and a resultant vector of the two components being generally towards the intersection of the first wall 144 and the second wall 146.

Figure 10:
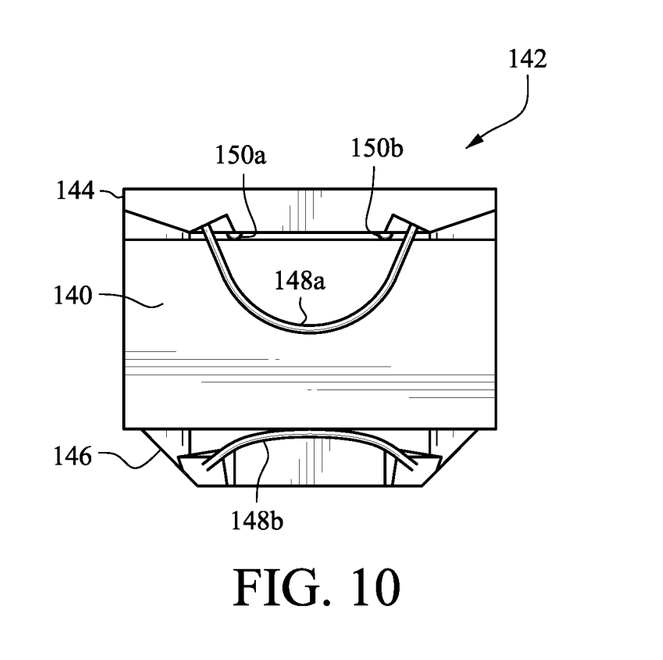
FIG. 10 is a second view of a second manner to provide a single translational degree of freedom.
Figure 11:
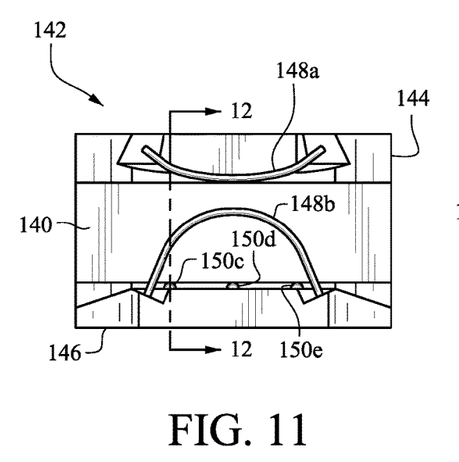
FIG. 11 is a third view of a second manner to provide a single translational degree of freedom.
Figure 12:
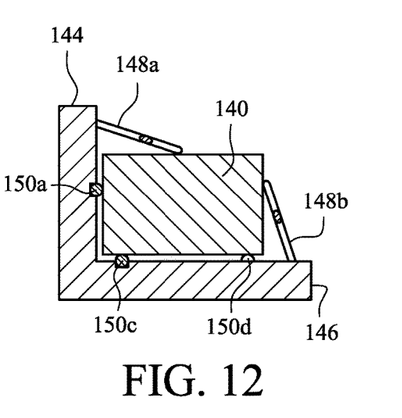
FIG. 12 is a fourth view of a second manner to provide a single translational degree of freedom.
Figure 13:
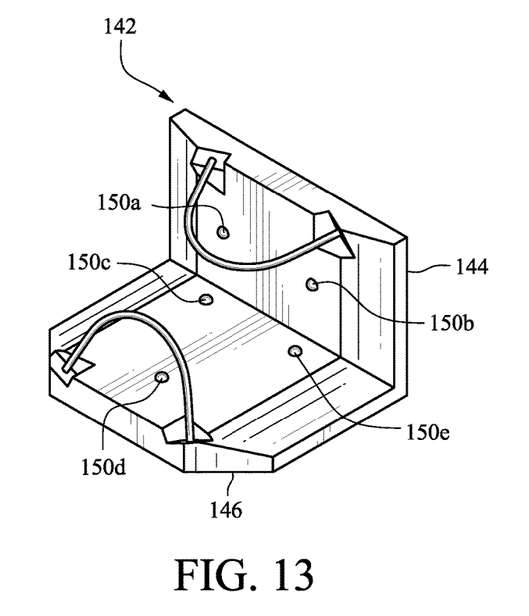
FIG. 13 is a fifth view of a second manner to provide a single translational degree of freedom.

FIG. 10 is a top view that differs from FIG. 9 only in that two spherical points of contact 150a, 150b are visible between the block 140 and the second wall 144. Similarly, FIG. 11 illustrates three spherical points of contact 150c, 150d, 150e that are not visible in FIG. 9. FIG. 12 illustrates a cross-section taken through FIG. 11 showing that the spherical points of contact may be in the form of balls. The balls may be fixed to provide sliding contact or allowed to roll and provide rolling contact. FIG. 13 illustrates the support member 142 without the block 140 so that all of the spherical points of contact 150a-150e are visible. Rollers 150c, 150d, 150e provide three points of contact along a bottom side of the block 140 and spherical points of contact 150a, 150b provide two points of contact along a side of the block 140.

With the configuration illustrated in these figures, the block 140 is constrained to move in a single degree of translational freedom that is parallel to both the first wall 144 and the second wall 146. Thus the block 140 may correspond to the intermediate portion 108.

Both of the configurations illustrated provide an intermediate portion 108 with a single degree of translational freedom and may provide a configuration that minimizes friction or drag due to the way in which the constraints are provided. With the minimal constraints on freedom described above, potential mechanical interference can be minimized and thus force necessary to translate along the single degree of freedom may be minimized as well. This may be beneficial in that no unnecessary forces should be transmitted to the optical fiber 100 and thus strain introduced to the fiber, which may affect the ability of the fiber to be used to accurately sense a shape of the tool, may be reduced or minimized.

Returning to FIG. 6, using shape sensing of the optical fiber 100, the adjustable bend 114 may be used to measure a relative position between the proximal end 104 and the intermediate portion 108 using shape sensing of the adjustable bend 114. Because the intermediate portion 108 is constrained to a single degree of translational freedom, the other five degrees of freedom are known. Thus the adjustable bend 114 can measure the sixth degree of freedom (the translational degree of freedom) so that all six degrees of freedom are known.

The adjustable bend 114 may also provide some spring-like restoring force and thus act as a return mechanism. If the force applied to constrain the intermediate portion 108 to a single degree of freedom is sufficiently low, the tendency of the adjustable bend 114 to return to a straight condition may provide sufficient force to urge the intermediate portion 108 to predetermined starting position. Thus as the body 116 is manipulated and the intermediate portion 108 is pulled away from the predetermined starting position, the adjustable bend 114 may provide sufficient restoring force to return the intermediate portion 108 to the predetermined starting position.

Figure 14:
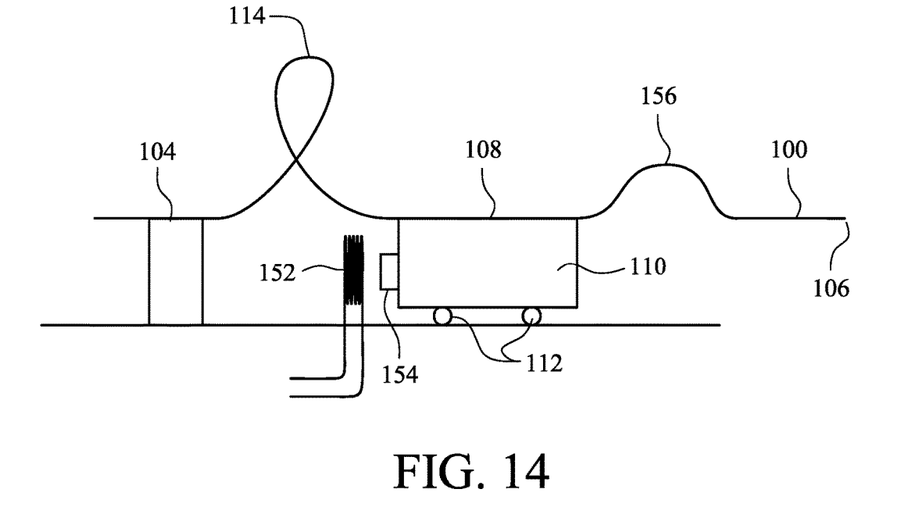
FIG. 14 is schematic representation of an optical fiber with a proximal end, a distal end, and intermediate portion and an electromagnet.

FIG. 14 illustrates an alternative to urge the intermediate portion 108 to the predetermined starting position. FIG. 14 is substantially the same as FIG. 6 except for the addition of an electric coil 152 and soft iron or magnet 154 (e.g., an electromagnet). With this configuration, a force can be applied with the electric coil 152 and soft iron or magnet 154. Because the optical fiber 100 is capable of providing very sensitive measure of strain in the fiber, as well as any buckling 156 that may occur, current in the electric coil 152 can be controlled based upon the measure of strain so that tension in the optical fiber 100 can be kept very low. Other implementations of the return mechanism can also be employed. For example, a spring (e.g., a coil spring) or pressurized gas (e.g., an air cylinder or air spring) could be used.

Figure 15:
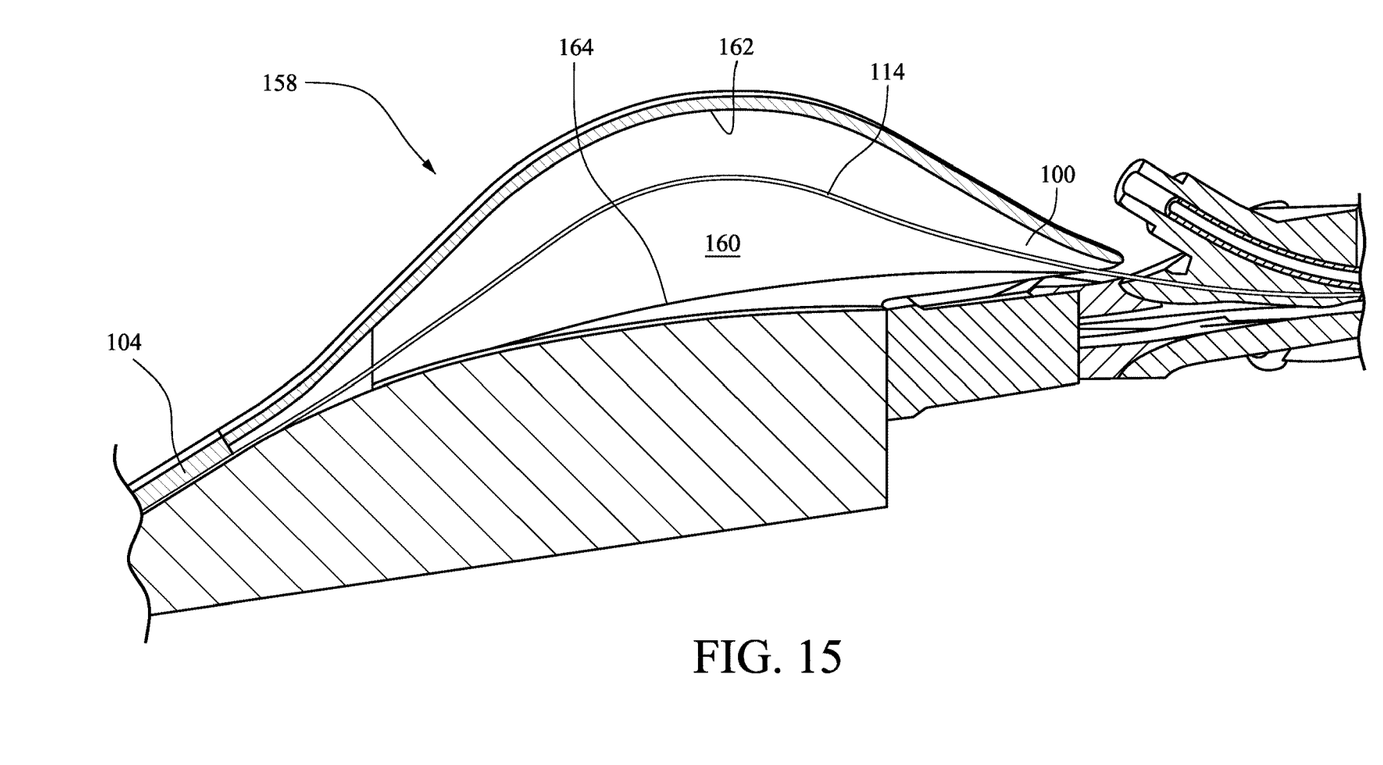
FIG. 15 is a first exemplary illustration of a housing that encloses an adjustable bend.

FIG. 15 illustrates the adjustable bend 114 within a housing 158, where the housing 158 is illustrated as a cross-section. In this figure, the adjustable bend 114 is illustrated as less than a complete loop and is approximately in the middle of a space 160 on the interior of the housing 158. The open space 160 includes an upper bound 162 (i.e., smallest bend radius) and a lower bound 164 (i.e., largest bend radius), illustrated as surfaces, which may limit an amount the curvature of the adjustable bend 114. For example, the upper bound 162 and the lower bound 164 may restrict how much the adjustable bend 114 can become relatively more bent or relatively more straight (e.g., adjust). This adjustment may accommodate the distance D described with respect to FIGS. 3 and 4 above that the optical fiber 100 may move relative to the catheter 10. As illustrated, space 160, the upper bound 162 and lower bound 164 together define a tall, narrow slot with an arched profile. However, any orientation of the space 160 can be utilized. For example, instead of the space 160 being on top, it could be on the bottom, sides, or anywhere in between. Also, the space 160 can be in forms other than a slot. Any shape can be utilized that allows the adjustable bend 114 to bend in a manner appropriate for the accuracy of measurement desired by the user while providing desired protection to the adjustable bend 114. But certain properties of the space 160 may provide advantages. For example, the tall, narrow slot illustrated may be more suitable for cleaning than a more expansive volume because the volume of the space 160 may be minimized and less cleaning fluid would be required when cleaning for surgical use.

As illustrated in FIG. 15, the adjustable bend 114 may be a gradual and/or gentle bend, e.g., a relatively large bend radius. The gentler the bend, the more accurate measurements with the fiber may be. However, a relatively gentler bend will require more space than a relatively less gentle bend. Thus size of the adjustable bend 114, and associated open space 160, can be optimized by trading accuracy of measurement for size, and vice-versa. If the adjustable bend 114 is sufficiently gradual (e.g., as illustrated in FIG. 15), it may be possible to achieve sufficiently accurate measurements without constraining a portion of the optical fiber 100 to a single degree of freedom. At least where the optical fiber 100 does not have a portion constrained to a single degree of freedom, the intermediate portion 108 described herein may refer to any part of the optical fiber 100 between the proximal end 104 and the distal end 106.

It may be preferable that the adjustable bend 114 does not contact either of the upper bound 162 or the lower bound 164 when the optical fiber 100 and/or catheter 10 is moved through the entire intended range of movement so that the adjustable bend 114 does not "bottom out." If the adjustable bend 114 contacts either upper bound 162 or the lower bound 164 during movement, strain could be induced in the optical fiber 100 and affect accuracy of measurement. To avoid this, clearance can be provided between the adjustable bend 114 and both the upper bound 162 and the lower bound 164 in a worst case (e.g., maximum adjustment) scenario.

In FIG. 15, the adjustable bend 114 is approximately half-way between the upper bound 162 and the lower bound 164, which corresponds to the optical fiber 100 in its straight (or most straight) position. When the optical fiber 100 bends with the catheter 10 (or other flexible tool) the adjustable bend 114 will move towards one of the upper bound 162 and the lower bound 164, and thus the adjustable bend 114 will become relatively straighter or relatively more bent.

Figure 16:
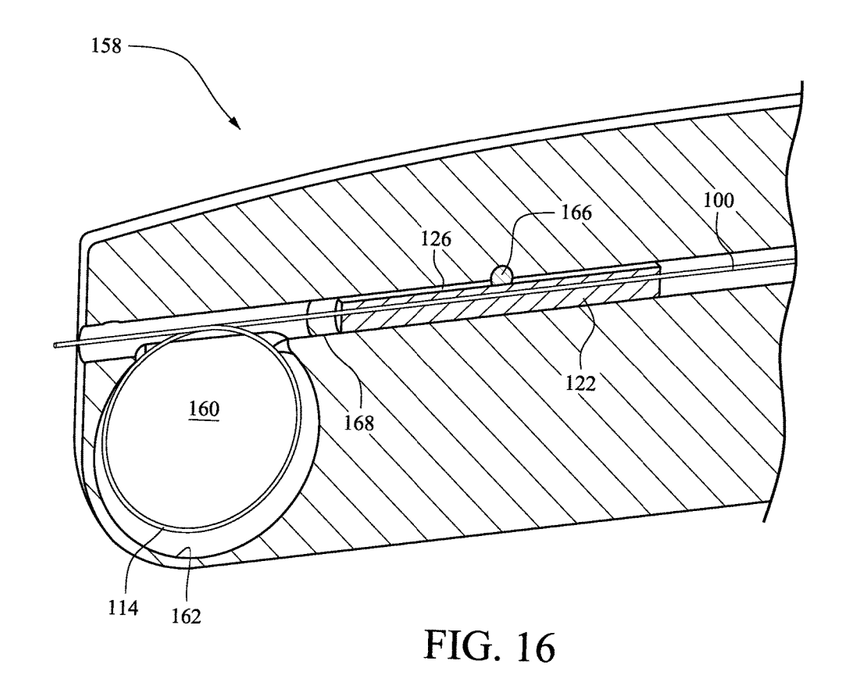
FIG. 16 is a second exemplary illustration of a housing that encloses an adjustable bend.

FIG. 16 illustrates (in cross-section) another example of the housing 158, which differs from FIG. 15 in that the adjustable bend 114 is a complete loop (e.g., 360°). Here, as the adjustable bend 114 adjusts, the diameter of the bend will increase or decrease. The open space 160 is illustrated as generally circular with the lower bound 162 being a diametrical surface of the open space. However, any convenient shape of the space may be chosen, so long as the space satisfies other design considerations. If the adjustable bend 114 is a complete loop, there may not be a need for an upper bound 164.

In FIG. 16, the complete loop is oriented substantially vertically. In other words, the complete loop is substantially within a vertically oriented plane. However, any orientation of the loop can be chosen.

FIG. 16 also illustrates a rigid member 122 substantially in the form of a cylinder with a flat 126 formed along an axial length of the cylinder. The flat 126 contacts a ball or cylindrical pin 166 (which may include another flat). Thus while moving within the cylindrical passage 168, the rigid member 122 may be constrained to substantially one degree of freedom. All of the other methods described above to constrain the intermediate portion 108 to a single degree of freedom (see, e.g., FIGS. 8-13 and the associated description) may be substituted for that illustrated in FIG. 16. If the optical fiber 100 has a portion that is constrained to a single degree of freedom, the portion constrained to a single degree of freedom can be used to calculate, simplify calculations of and/or improve accuracy of calculation of the shape and orientation of the optical fiber 100 between the single degree of freedom portion and the distal end 106. The adjustable bend 114 can be used to calculate or measure the location of the portion constrained to a single degree of freedom, where orientation is known based upon the single degree of freedom. Then the location and orientation of the optical fiber 100 from the single degree of freedom portion and up to and including the distal end 106 can be calculated based upon the location and orientation of the single degree of freedom portion.

Figure 17A:
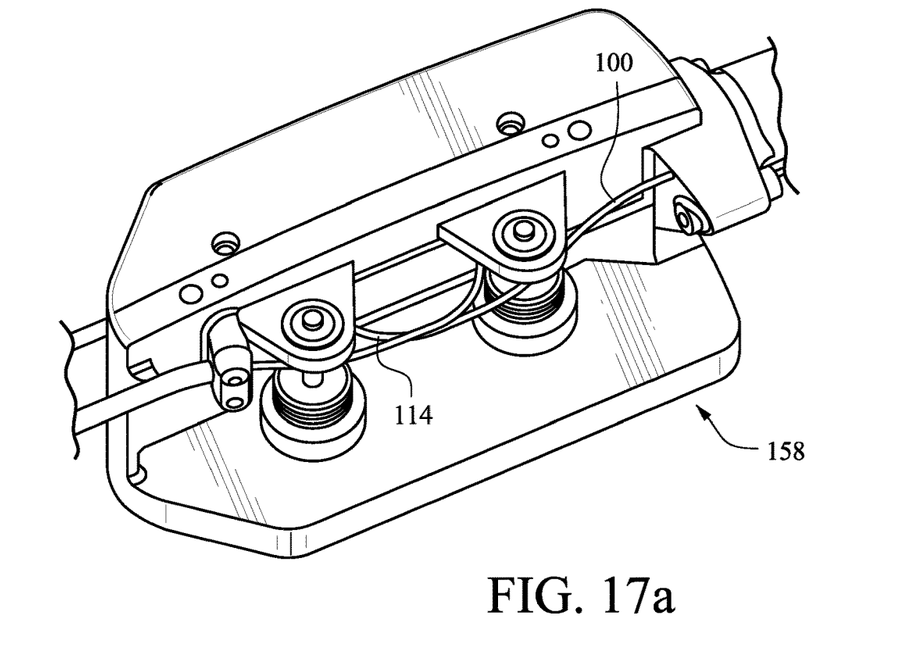
FIG. 17a is a third exemplary illustration of a housing that encloses an adjustable bend.
Figure 17B:
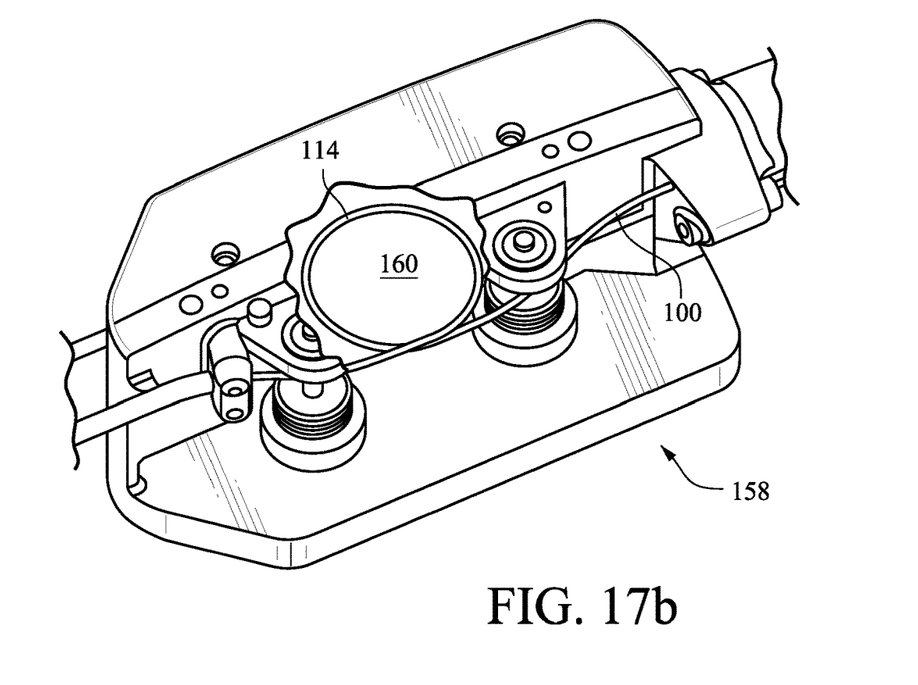
FIG. 17b is similar to FIG. 17a but includes a broken-out portion so that the adjustable bend is more visible.

FIGS. 17a and 17b are similar to FIG. 16 in that the adjustable bend 114 is in the form of a loop. Here, the loop is illustrated as horizontal and the open space 160 is not distinctly bounded. Instead, the open space takes advantage of an open volume that is not otherwise used. Thus there may also be no distinct upper bound or lower bound. The housing 158 may include a cover, which is not illustrated so that the interior is visible. The proximal end 104 (not illustrated in this figure) may be fixed near the adjustable bend 114 and serve as a reference location for calculating the shape of the optical fiber 100 or a single degree of freedom can be applied (as illustrated in FIGS. 9-13 and 16).

Figure 18:
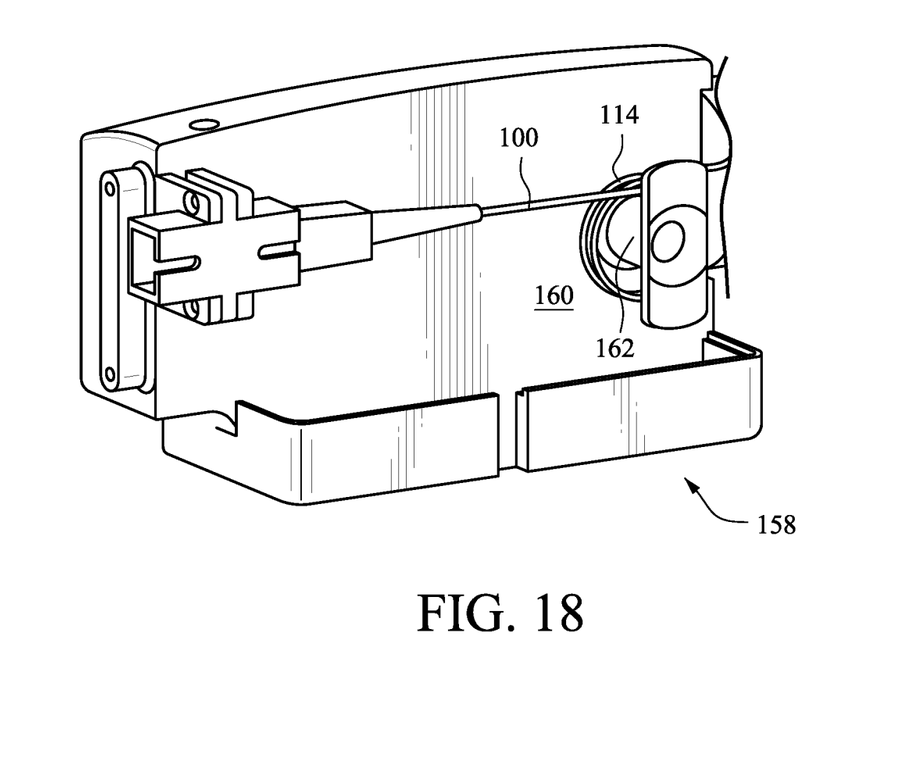
FIG. 18 is a fourth exemplary illustration of a housing that encloses an adjustable bend.

FIG. 18 is similar to FIG. 16 in that the adjustable bend 114 is substantially vertical. However, the adjustable bend 114 includes a plurality of complete loops. As illustrated, there are two complete loops (e.g., 720°). Also, the open space 160 is illustrated with an upper bound 162 (in the form of a cylinder that limits a minimum bend radius) but without a distinct upper bound. In this configuration, the upper bound also provides support and/or positional location for the adjustable bend 114. The housing 158 may include a cover, which is not illustrated so that the interior is visible. This configuration can also be used with a single degree of freedom portion and/or a fixed portion as described above with respect to the proximal end 104.

Including more than one complete loop may be advantageous in that the diameter of the loops does not have to change as much as a single loop for the same about of distance D that the optical fiber 100 moves. For example, assuming that the loop is a circle, the diameter of a loop (d) relates to the circumference (C) with the well-known equation C=πd. If the loop needs to accommodate the optical fiber moving a distance D, then the circumference will increase or decrease by D (C±D=πd). This leads to the diameter of the circle varying by ±D/π. However, with two loops, the change is over two loops and thus the diameter would only need to accommodate ±D/2π. Increasing the number of loops to three would result in ±D/3π. Thus the amount that the diameter will change is inversely proportional to the number of loops, and more loops will require less space for the diameter to adjust, which could result in a more compact device.

For each implementation of the open space 160 described above, the amount of clearance around the adjustable bend 114 may be optimized based upon several factors. If the adjustable bend 114 can be constrained to allow movement only in one plane (e.g., only in the x and y directions of a Cartesian coordinate system, but not the z direction), the accuracy of measurements made with the optical fiber 100 may be increased because any associated calculations could take that limited movement into account. However, the application of such planar constraint would likely require contact with the optical fiber 100 that, with any associated friction, would cause drag that induces strain in the fiber. But this strain could alter the calculation used to sense the shape of the fiber.

If a frictionless system is not practical, it may be practical to provide a clearance around the adjustable bend 114 that eliminates, or substantially reduces, contact between the adjustable bend 114 and the nearest wall. This may be achieved by providing a gap between adjacent walls that is greater than the diameter or thickness of the optical fiber 100 (e.g., the open space 160 within the housing 158 is sufficient to provide radial clearance around an entire perimeter of the adjustable bend 114 along a predetermined length of the adjustable bend 114). With a limited amount of clearance, the adjustable bend 114 can be constrained to be substantially within a plane. For example, if the gap between adjacent walls is slightly greater than the thickness or diameter of the optical fiber 100 up to twice the thickness or diameter of the optical fiber 100, the adjustable bend 114 may be constrained to within substantially a plane.

Each of the housings 158 described above can prevent contact with the adjustable bend 114 from outside of the housing 158. For example, a user would be prevented from inadvertent contact with the adjustable bend 114 that deforms the adjustable bend 114, which could change the detected shape of the optical fiber 100. Thus the adjustable bend 114 can adjust only due to, or substantially only due to, the change in the distance D described above.

In each of the configurations discussed above, it may be preferable to prevent axial strain in the optical fiber 100 from exceeding 500 microstrain, more preferably 50 microstrain, and/or prevent the optical fiber 100 from having a bend radius less than 0.3 inches, more preferably prevent the optical fiber 100 from having a bend radius less than 3 inches.

While the present technology has been described in connection with several practical examples, it is to be understood that the technology is not to be limited to the disclosed examples, but on the contrary, is intended to cover various modifications and equivalent arrangements included within the spirit and scope of the technology.

The invention claimed is:

1. A flexible tool comprising:
   an optical fiber including
   a proximal end,
   a distal end,
   an intermediate portion between the proximal end and the distal end, and
   an adjustable bend between the proximal end and the intermediate portion; and
   a rigid member, wherein the intermediate portion is fixed within the rigid member, and wherein the rigid member is substantially a cylinder with a flat surface along an axial length of the cylinder,
   wherein the intermediate portion is constrained to have a single degree of freedom that is translational substantially along an axis defined by the optical fiber at the intermediate portion.

2. The flexible tool according to claim 1, further comprising a body including a flexible portion and a free end, wherein a portion of the optical fiber is within the body and the distal end is fixed relative to the body at or near the free end.

3. The flexible tool according to claim 2, wherein the body includes a neutral axis and the optical fiber is disposed within the body offset from and substantially parallel to the neutral axis at least at the flexible portion.

4. The flexible tool according to claim 2, wherein the distal end is movable with three degrees of translational freedom and two degrees of rotational freedom with respect to the proximal end.

5. The flexible tool according to claim 2, wherein the flexible portion includes a flexible joint.

6. The flexible tool according to claim 1, further comprising:
   two first cylindrical pins with first central axes that are substantially parallel to one another and together define a first plane;
   a second cylindrical pin with a second central axis that is in a second plane that is substantially parallel to and offset from the flat surface and that is substantially normal to the first plane;
   a ball; and
   a spring, wherein the second cylindrical pin and the ball are in contact with the rigid member along the flat surface, wherein the two first cylindrical pins are in contact with the rigid member along the axial length of the cylinder but not on the flat surface, and wherein the spring contacts the rigid member to urge the rigid member into contact with the two first cylindrical pins, the second cylindrical pin, and the ball.

7. The flexible tool according to claim 1, wherein the rigid member comprises a block with a first flat surface defined by a first plane and a second flat surface defined by a second plane that intersects the first plane along a line that is substantially parallel to the single degree of freedom.

8. The flexible tool according to claim 7, further comprising a support member with three spherical points of contact that contact the first flat surface, two spherical points of contact that contact the second flat surface and an urging member that urges the first flat surface and second flat surface into respective contact with the three spherical points of contact and the two spherical points of contact.

9. The flexible tool according to claim 8, wherein the rigid member includes a third flat surface substantially parallel to the first flat surface and a fourth flat surface substantially parallel to the second flat surface, and the urging member includes a first member that contacts the third flat surface to urge the rigid member towards the three spherical points of contact and a second member that contacts the fourth flat surface to urge the rigid member towards the two spherical points of contact.

10. The flexible tool according to claim 1, further comprising a return mechanism that is configured to urge the intermediate portion towards a predetermined starting location.

11. A method for detecting a shape of a flexible tool, the method comprising:
    disposing an optical fiber along at least a portion of the flexible tool;
    fixing a first end of the optical fiber at or near an end of the flexible tool;
    fixing a second end of the optical fiber at a known position;
    constraining an intermediate portion of the optical fiber between the first end and the second end to a single degree of translational freedom substantially along an axis defined by the optical fiber, wherein constraining the intermediate portion of the optical fiber includes contacting a flat surface along an axial length of a rigid member, wherein the intermediate portion is fixed within the rigid member, and wherein the rigid member is substantially a cylinder;
    moving at least the end of the flexible tool so that the flexible tool has a resultant shape;
    transmitting light along the optical fiber; and
    detecting the resultant shape of the flexible tool using the transmitted light.

12. A flexible tool comprising:
    an optical fiber including:
    a proximal end,
    a distal end,
    an intermediate portion between the proximal end and the distal end, and
    an adjustable bend between the proximal end and the intermediate portion; and
    a rigid member, wherein the intermediate portion is fixed within the rigid member, and wherein the rigid member is substantially a cylinder with a flat surface along an axial length of the cylinder; and
    a housing that encloses the adjustable bend and provides space within the housing for the adjustable bend to adjust, wherein the intermediate portion is constrained to have a single degree of freedom that is translational substantially along an axis defined by the optical fiber at the intermediate portion.

13. The flexible tool according to claim 12, wherein the housing prevents contact with the adjustable bend from exterior to the flexible tool.

14. The flexible tool according to claim 12, wherein the adjustable bend includes at least one complete loop.

15. The flexible tool according to claim 12, wherein the adjustable bend is less than one complete loop.

16. The flexible tool according to claim 12, wherein the housing provides a clearance to allow relative bending and straightening of the adjustable bend, and the flexible tool is configured to bend a predetermined positive angle within the intermediate portion and a predetermined negative angle within the intermediate portion; and the clearance accommodates an entire extent of relative bending and straightening within the adjustable bend that is caused by bending the flexible tool the predetermined positive angle and the predetermined negative angle.

17. The flexible tool according to claim 12, wherein the space within the housing is sufficient to provide radial clearance around an entire perimeter of the adjustable bend along a predetermined length of the adjustable bend.

18. The flexible tool according to claim 12, wherein the space within the housing constrains the adjustable bend to be substantially within a plane.

* * * * *